US012565636B2

(12) United States Patent
Zhu et al.

(10) Patent No.:     US 12,565,636 B2
(45) Date of Patent:          Mar. 3, 2026

(54) METHOD FOR DETECTING COMPOSITION OF FERMENTATION GAS OF GUT FLORA AND INSTRUMENT THEREFOR

(71) Applicants:SUZHOU HALO BIOTECHNOLOGY CO., LTD., Suzhou (CN); HANGZHOU HALO MEDICAL TECHNOLOGY CO., LTD., Hangzhou (CN)

(72) Inventors: Liying Zhu, Hangzhou (CN); Yu Du, Hangzhou (CN); Jieying Chen, Hangzhou (CN); Lei Lei, Hangzhou (CN); Xin Wang, Hangzhou (CN); Xianglong Li, Hangzhou (CN)

(73) Assignees: SUZHOU HALO BIOTECHNOLOGY CO., LTD., Suzhou (CN); HANGZHOU HALO MEDICAL TECHNOLOGY CO., LTD, Hangzhou (CN)

( * ) Notice: Subject to any disclaimer, the term of this patent is extended or adjusted under 35 U.S.C. 154(b) by 498 days.

(21) Appl. No.:     18/246,160

(22) PCT Filed:     Jul. 26, 2021

(86) PCT No.:     PCT/CN2021/108331
§ 371 (c)(1),
(2) Date:     Mar. 21, 2023

(87) PCT Pub. No.: WO2022/062626
PCT Pub. Date: Mar. 31, 2022

(65) Prior Publication Data
US 2023/0357701 A1     Nov. 9, 2023

(30) Foreign Application Priority Data
Sep. 28, 2020     (CN) .......................... 202022180123.1
Jun. 21, 2021     (CN) ........................ 202110686195.X

(51) Int. Cl.
*C12M 1/34*          (2006.01)
(52) U.S. Cl.
CPC .................................... *C12M 41/34* (2013.01)
(58) Field of Classification Search
CPC ...... C12M 41/34; C12M 41/00; C12M 41/26; C12M 41/18; C12M 29/06; C12M 29/24;
(Continued)

(56) References Cited

U.S. PATENT DOCUMENTS

2013/0059371 A1*   3/2013   Shevitz .................. C12M 29/04
                                                                      210/257.2
2017/0349874 A1*   12/2017   Jaques .................. B01F 27/191

FOREIGN PATENT DOCUMENTS

CN          101113947 A        1/2008
CN          102399692 A        4/2012
(Continued)

*Primary Examiner* — Michael L Hobbs
(74) *Attorney, Agent, or Firm* — MUNCY, GEISSLER, OLDS & LOWE, P.C.

(57)          ABSTRACT
A method for testing gas produced by fermentation of intestinal flora includes placing a sample bottle into a sample bin; inserting the sampling needle into a sample bottle for sampling; communicating the sample bottle with a gas detecting cavity, and quantitatively extracting the fermentation gas from the sample bottle; detecting the concentration of a certain fermentation gas using a sensor to deduce the concentration of the fermentation gas in the sample bottle; repeating the detection by using a step-type injection mode until the detection in preset gradients of all the fermentation gas of gut flora is completed, and the detection data of each fermentation gas of gut flora conforms to the detection range of the preset gas sensor; and carrying out reduced calculation of the concentration of each fermentation gas of gut flora in the sample bottle according to the collected data. An instrument carries the test method.

9 Claims, 2 Drawing Sheets

(58) Field of Classification Search
    CPC ...... C12M 29/18; C12M 29/14; C12M 21/16;
                C12M 23/34; C12M 45/09; C12P 5/023;
                                              Y02E 50/343
    See application file for complete search history.

(56)                  References Cited

FOREIGN PATENT DOCUMENTS

| | | | |
|---|---|---|---|
| CN | 102787067 | A | 11/2012 |
| CN | 103740589 | A | 4/2014 |
| CN | 104266895 | A | 1/2015 |
| CN | 110819526 | A | 2/2020 |
| CN | 111676127 | A | 9/2020 |
| ES | 2322307 | A1 | 6/2009 |
| WO | WO1994009895 | A1 | 5/1994 |

* cited by examiner

METHOD FOR DETECTING COMPOSITION OF FERMENTATION GAS OF GUT FLORA AND INSTRUMENT THEREFOR

TECHNICAL FIELD

The present invention relates to a method for detecting the composition of gut flora fermentation gas and an instrument thereof, in particular to a method and an instrument for detecting the fermentation gas of colonic flora.

BACKGROUND

There are two large class metabolites of the gut flora, short-chain fatty acids (SCFA) and gases. It is well known that gut flora is a key factor that affects human health, and this effect is mainly achieved by regulating the physiological function of the human body by means of its metabolite. It is known at present that a relatively clear function of SCFA is to participate in the energy metabolism of the human body, the homeostasis maintenance of blood glucose, the regulation of appetite and temperature, and blood pressure, and SCFA is a key for maintaining function of intestinal barrier and immune of intestinal tract and whole body. In contrast, the gases, primarily hydrogen, methane, carbon dioxide, hydrogen sulfide, and the like, may not affect the physiological function of the human body, but the correlation with the disease is relatively clear, mainly the dyspepsia of the carbohydrate and the constipation related to the methane. This cognition is primarily benefited from the clinical application of the breath test. The test is mainly used for detecting the gas content such as hydrogen and methane in exhaled breath of a subject to realize indirect analysis of microbial gas production in the small intestine as a judgment basis for diseases. This clinical test method begins in the 1970s, which is currently adopted by North American consensus as a suggested diagnosis basis for excessive growth of small intestine bacteria, dyspepsia of carbohydrate, and constipation related to methane. However, there are few clinical applications for the analysis of colon microbial gas production.

The colon is the primary settlement site of the gut flora, and the number of microorganisms in the colon is 1010 to 1013, up to 100 million times as compared to the number of microorganisms in the small intestine (104-107). The mentioned intestinal flora generally refers to the microorganisms of the colon, so the metabolites produced by the microorganisms of the colon, including gas, are also much more than the yield of the small intestine bacteria. About 1.2 liters of gas per day produced by colon microorganism, which is released through two main pathways, one is absorbed by the intestinal wall into the blood and exhausted out by breath, and the other is moved towards the distal end of the colon along with the intestinal contents so as to be discharged from the anus. Therefore, the gas generated by the gut flora in the colon may not be quantitatively detected by the breath test due to a huge amount of gas production and different release pathways. However, directly collecting gas from the colon is an invasive surgery, which may be feasible in individual clinical cases, but it is unlikely to become a method for scientific research samples. It can be seen that the difficulty of gas collection results in serious hysteresis in the study of gut flora gas. The gas produced by the gut flora, as the two large class metabolites of the gut flora along with SCFA, has little research and lack of data, which will certainly cause one-sided and insufficient understanding of metabolites of the gut flora, thus distorting our understanding of the relationship between gut flora and diseases.

The gut flora is referred to as a second genome of the human, but different from the high stability of human genome, it is highly plastic and mainly affected by environmental factors, including birth mode, breastfeeding, diet, antibiotic usage history and the like. The diet is a major factor which changes the composition of gut flora and its metabolites (David, Nature, 2014). The incidence rate of chronic diseases such as immune-related diseases, cancers, metabolic diseases and the like continuously rises in recent 50 years, and the trend is highly consistent with the change of diet and lifestyle, indicating that the gut flora plays an important role in the occurrence and development of the diseases (David, Nature, 2014). On the other hand, the high plasticity of the intestinal flora is also enabled to become a major target for the treatment and prevention of these modern chronic diseases (Genitile, Science, 2018). This high plasticity also contributes to the great differences in gut flora among individual. Therefore, the gut flora is considered to be the subject of precise medicine, and the personalized detection becomes the basis for implementing precise medicine. At present, the detection of metabolites of the gut flora is still a blank in the field of clinical examination.

Traditional research on gut flora is mainly conducted in human subject. Due to the inherent limitations of human trials, such as poor compliance, long time consumption, high cost, etc. so that other research methods, such as in vitro models, ex vivo models, computer simulations, animal intestinal models and the like are increasingly paid attention. Compared with a labor- and time-consuming human trial and animal test, in vitro model, as known as in vitro simulated fermentation model, has rapid and high-throughput features, which has broad application scenarios in clinical and various scientific research fields. Therefore, based on the in vitro batch fermentation method, we developed a set of metabolites detection system for gut flora to meet the urgent needs of clinical and scientific research for rapid and high-throughput detection technology.

The main method for studying gut flora is human experiment trial, due to the limitations of time- and labor-consuming, poor compliance and the like, in vitro models, ex vivo models, computer simulation and animal intestinal model systems provide another large-class of methods for studying gut flora. It has long been proposed that while the gut flora being regarded as an organ capable of complex metabolism, it should be considered that overall research may be carried out in vitro (Macfarlane & Macarlane, Curr Opin Biobac, 2007). Nowadays, animal experiments are also limited because of ethics, host specificity and other conditions, so the advantages of in vitro intestinal model have become increasingly prominent. Based on the simulation of the growth environment of gut flora in the digestive tract, the gut flora in feces is used to establish a simulated fermentation system in vitro, which is divided into two types: a continuous fermentation model and a batch fermentation model. The continuous fermentation model is an open system that simulates the food intake of human intestinal tract and the excretion of feces, involving the flow control of medium, pH control and anaerobic control of the whole fermentation system and the like, the equipment is large and complex, but the overall composition of the gut flora is well simulated, so that the similarity of the model is high, it may also simulate the fermentation of different parts of the human colon such as ascending colon, transverse colon and descending colon through multi-stage series. The models with a wide range applications are three-stage continuous colon model system (SANGNSIDDAPA, Ozoonone, 2011), and a full digestive tract simulation system involving the stomach, small intestine and colon, such as a SHIME model (Van den Abbeele, Appl. Environ. Microbiol. 2010) and TIM model. (Reis, Food Biophys 2008), etc. Williams et al. successfully analyze the pharmacokinetic parameters of the drug using TIM-1 and TIM-2 (Williams, Annu Rev Food Sci. L, 2015), showing a potential broad application prospect of the continuous fermentation model. We also have a Chinese patent (ZL201711069219.7) of a continuous fermentation system.

On the other hand, the batch fermentation model mainly simulates the far-end colon, which is characterized by simple equipment and short fermentation time. Although the degree of simulation is less than that of a continuous fermentation model, there is a great advantage in the rapid analysis of metabolites, not only a fast speed but also a high throughput. The method has been used for in vitro evaluation of multiple prebiotics and the study of different food components on gut flora growth and metabolites thereof, including SCFAs and gas production (Wang & Gibson, J. Appl. Bacteriol. 1993; Vulevic, Am J Clin Nutr, 2008). By combining batch fermentation models with 16S sequencing, we also find differences in metabolism of different intestinal types on long-chain isomalto-oligosaccharides (IMO), including the promotion of *Bifidobacterium* by SCFAs (WU, Anaerobe, 2017). However, there are also many problems in the application of batch simulation fermentation.

Compared with the difficulty of collecting intestinal gas in human trials or animal experiments, the collection of gut flora fermentation gas is no longer a problem for batch fermentation model. However, there are still many difficulties in the application of gas detection of batch fermentation in clinical detection, and there is a lack of simple and reliable methods. Firstly, the detection equipment for environmental gas is not applicable completely, and this equipment often require several liters of gas, so as to pump the environmental gas into the detection chamber in a circulating manner, while the gas in the detection chamber reaches equilibrium with the environmental gas, the sensor will carry out the detection of the gas content. Or an enlarged space, such as about 1 meter of optical path, is required in order to utilize a variety of analytical instruments for gas detection, such as gas within a large chimney. Detection of gas in a 10 mL penicillin bottle filled with a 5 mL liquid culture medium is generally adopted in clinical detection, and the detection object is the gas composition in a 6.7 mL physical space. This is a challenge for all existing gas detection equipment; therefore, the detection equipment for environmental gas may not be used to implement the detection of the small amount of gas encountered by the present invention.

Secondly, the prior art cannot collect gas at a time to detect the components of various gut flora fermentation gases. Usually, the gas chromatography is used to detect the fermentation gas, and if only hydrogen and methane are detected, one flame detector may be used to detect them simultaneously, however, with the addition of hydrogen sulfide and carbon dioxide, the detection of 4 gases requires at least two detectors, and the gas needs to be injected twice, which requires more gas. Generally, a closed container of more than 200 ml is used to perform in-vitro simulated fermentation, and a syringe is used to collect gas samples and manually inject samples for detection. However, clinical detection deal with less than 10 ml of space, and there are many extreme cases among clinical samples. Some special samples, such as those from newborns, may not produce enough gas to be extracted with a syringe, so they may not be detected by manual injection gas chromatography. In addition, manual injection of gas chromatography has a large error in detection. Meanwhile, due to the fact that hydrogen which is extremely easy to escape and hydrogen sulfide with active chemical properties exist in the fermentation gas, multiple sampling will cause great losses leading to errors. Therefore, a common gas chromatography detection method may not detect four gases including methane, hydrogen, carbon dioxide and hydrogen sulfide at one time, and the detection error is large, which may not be qualified for the detection of a small amount of gas in fermentation vials used for clinical detection.

For example, in 2020, researchers at the University of Minnesota in the United States analyzed the relationship between the abundance of methane-producing bacteria in human gut flora and methane production by detecting the amount of methane produced by in vitro fermentation. In this study, methane was detected by gas chromatography and then hydrogen sulfide was detected by environmental gas detection equipment, the QRAE3 gas monitoring unit (RAE Systems, San Jose, CA). The requirement of the gas chromatography on the sample amount is not high, only 2 ml is needed, while the detection of hydrogen sulfide requires the extraction of 58 ml of fermentation gas, and then put into a container to dilute 5 times to 348 ml of gas, and then a specific equipment is used to detect the content of hydrogen sulfide (Teigen, Dig Dis Sci, 2020). Such cumbersome operation is also because there is no expediency for good detection equipment. Due to the fact that the chemical property of hydrogen sulfide is very active, gas chromatography detection may be adopted theoretically, but the corrosive nature of hydrogen sulfide will cause considerable damage to the detection equipment, moreover, the content of hydrogen sulfide is high after fermentation of gut flora, so gas chromatography is not suitable for the detection of fermentation gas of colonic gut flora.

Thirdly, although researchers try to develop special equipment capable of detecting gut flora gas, the detection range of an existing sensor for detecting the gas concentration may not adapt to the concentration fluctuation range of human fermentation gas of gut flora, and the detection effect is poor. A sensor that detects a gas concentration is either suitable for a small range or a wide range. In order to obtain the sensitivity of the gas concentration in a small range, a small-range sensor needs to be used, but the small range sensor will fail because of exceeding the range while the gas concentration is high; conversely, the sensor with large range lacks the sensitivity and accuracy of small range in gas concentration detection.

Based on a batch fermentation model, Australian scientists have developed an in vitro fecal fermentation system with gas and pressure sensors for real-time monitoring of fermentation gases (Robart, Sensos and Actuatoprs B: Chemical, 2017). A 200 ml bottle containing 10 ml of culture medium and 50 ml of fecal suspension (16%) is used in this system, the bottle mouth being mounted with a gas sensor and a release valve device from bottom to top, the former being used to detect four gases, such as hydrogen, methane, carbon dioxide, and hydrogen sulfide, in gas content, the latter being used to maintain a constant pressure of the fermentation system. By using the device to monitor 4 h in vitro fermentation data of human gut flora, researchers found that generation of hydrogen sulfide is more easily induced by cysteine than inorganic sulfide, but strongly inhibited by non-digestible carbohydrates such as resistant starch and fructo-oligosaccharides (FOS) (Yao, Gut Microbes, 2018). However, this real-time detection device can accurately detect the fermentation gas from 0 to 4 hours, which also means that the fermentation gas content may not be detected for a long time, such as 24 hours, because the gas content will increase out of the sensor range. The content of hydrogen and methane in human intestinal gas is very high, which may exceed the limit value of explosion, as the fire in the operating room is a very good illustration.

For the above reasons, although the importance of metabolites of gut flora has been recognized by the academic community as the main medium of gut flora affecting human health, but in the two existing large metabolites, only SCFA data is relatively easy to obtain, while the content of gas is no well detected. However, missing half of the metabolic data is very detrimental to the comprehensive understanding of the impact of gut flora on the human body. Therefore, the development of detection equipment for the fermentation gas of gut flora has become an urgent task for further research on gut flora.

SUMMARY OF THE INVENTION

The invention aims to overcomes the shortcomings of the prior art and provides a simple and rapid detection method for the composition of fermentation gas of gut flora and an instrument thereof, which is suitable for clinical detection. In the present invention, the concentration of four gases including methane, hydrogen, carbon dioxide, hydrogen sulfide and the like in the fermentation gas of gut flora may be detected through one time gas injection, and the limitation of the sensor range is overcome.

The present invention adopts the medium of continuous fermentation model which has a better simulation effect of colonic fermentation to create an environment which is beneficial to the growth of intestinal flora as possible, in addition, the relatively fixed medium is used to provide a stable fermentation environment to compare the growth status of different gut flora, including flora composition and metabolites, so as to find out the generality among them and further understand the effects of various dietary components on gut flora, which promote the development of precision nutrition and precision medicine. Meanwhile, this fermentation system, with the characteristics of rapid, accurate and high-throughput, may meet the actual needs of scientific research and clinic practice. To this end, we constructed a small batch fermentation system by using the medium of continuous fermentation model and developed an analytical equipment to detect small amount of gas produced by gut flora in this batch fermentation system.

Firstly, a set of metabolite detection systems based on batch fermentation models capable of simultaneously detecting SCFA and gas is developed. In order to meet the needs of rapid, accurate and high throughput in clinical practice, a small-scale batch fermentation model is designed, and the professional gas analysis method and equipment for fermentation gas are customized for the model in the present invention, while the timeliness of the clinical detection equipment is achieved.

According to the present invention, a relatively small fermentation system is used to reduce the sample amount: 5 mL of a culture medium is added to a 10 mL penicillin bottle, and a 5 mL batch fermentation system is established by using an anaerobic filling technique. The in vitro stimulated fermentation of gut flora generally adopts a suspension of human feces, which the total inoculation rate is 1% (w/v). Due to the small system, the fermentation vial of the present invention requires little amount of sample, each vial only needs 0.05 g of feces, and more than 10 bottles of culture medium may be inoculated by collecting 1 g of feces.

In addition, given that there is no fixed medium for the batch fermentation model at present, the conventional medium of the continuous fermentation model is adopted in the present invention to maintain the consistency of the nutrient source in the in vitro simulation system. Usually, the common batch fermentation model adopts the buffer solution of inorganic salt, and the main organic matters come from fecal residues, which lead to a serious shortage of nutrient sources for gut flora and a decrease in similarity to the colonic fermentation environment. The individual differences in gut flora are relatively large, and if there are differences in the composition of organic matters in the culture medium, the randomness of differences in metabolites produced by in vitro fermentation may be exacerbated. Therefore, the usage of the recognized culture medium by the gut flora is beneficial to reduce the non-predictive fluctuations of the detection data.

According to the small characteristics of the batch fermentation model system, there is about 6.7 ml physical space in the fermentation vial to store the fermentation gas, so the present invention provides a series of technologies to detect the content of four gas components under the condition of small amount of gas, including hydrogen, methane, carbon dioxide and hydrogen sulfide.

The scheme of inventive concept is as follows:

1. YCFA, a medium commonly used for culture of gut flora, is used as the basic medium, and a study on the influence of a target carbon source on gut flora is carried out by adding the carbon source.

2. In order to solve the difficulties caused by the small amount of detectable gas, two designs are made:

a) Firstly, a sample chamber capable of accommodating the entire fermentation vial is designed to directly detect the gas in the fermentation vial and reduce the distance between the sample vial and the detection chamber.

b) The equilibrium between the detection chamber and the sample gas is established by the using vacuum. To detect the gas by using a sensor, it is necessary to form a gas environment by an air pump in the detection chamber that is consistent with the sample gas, so that a sufficient amount of gas is required, otherwise the consistency of the gas in the detection chamber and the sample gas is difficult to achieve. According to the present invention, the vacuum degree of the detection chamber is used to dilute the gas with a certain dilution times by quantitatively extracting the fermentation gas in the sample vial, and then the content of diluted gas is converted into the gas content in the fermentation vial by the ideal gas law. To this end, we first detected the gas pressure in the fermentation vial, as well as the gas density and other parameters before extracting the fermentation gas. This design scheme greatly reduces the required amount of the sample gas, which solves the problem of the consistency of the gas in the detection chamber and the sample vial.

3. In the development process, it is found that there are large individual differences, of which a certain gas content of one sample exceeds the measurement range of the gas sensor among ten detected sample, which seriously affects the accuracy of detection. In addition, we found that the content of certain gases in patients with some diseases is generally higher than that in normal people, such as hydrogen sulfide, the content of patients with inflammatory bowel disease is higher than that of normal people, so that the sensor for hydrogen sulfide capable of detecting normal people is unsuitable for the fermentation gas of such patients.

Therefore, the invention adopts a gradient injection method to solve these problems at one stroke. A small range/high precision sensor is employed to simultaneously achieve high precision and wide range detection. The percentage (1%-99%) of gas entering the chamber was controlled by adjusting the initial pressure of the chamber to expand the existing detection range and detection accuracy of the sensor, which may accommodate the great differences in the composition of fermentation gas samples among individuals. By adopting the gradient injection method, for example, the fermentation gas is extracted 4 times continuously, each time accounting for 1%, 5%, 10% and 84% of the total fermentation gas, so that the detection results within the sensor range can always be found in several times injection, and the gas composition in the fermentation vial is converted by using these detection results, The volume of the gas collected each time is obtained by calculating the air pressure value read by the barometer. Meanwhile, this method also solves the problem that the concentration of different gases in the same sample varies greatly, which may not be accurately measured simultaneously by the existing sensors.

In the following description, the fermentation vial is also called the sample vial. A method for detecting composition of fermentation gas of gut flora comprises:

S1. Opening the sample chamber, placing the fermented sample vial into the sample chamber, and closing the sample chamber;

S2. Inserting the sampling needle into the sample vial, detecting the air pressure P0 of the sample vial by using a first air pressure sensor, and converting the total amount of the fermentation gas to $\Delta V = V1(P0/Patm-1)$, wherein V1 is the volume of the sample vial, and the Patm is atmospheric pressure, namely the pressure of the sample vial before fermentation.

S3. The pressure of sample vial reaching the first pressure P1 by using the air pump connected to sample vial, the pressure of gas detection chamber reaching the second pressure P2 by using the vacuum generator connected to gas detection chamber, and then communicating the sample vial and the gas detection chamber to quantitatively extract the fermentation gas from the sample vial, so that the proportion of the fermentation gas entering the gas detection chamber reaches the first gradient; the proportion of gas entering the gas detection chamber is $(P1-P2)*V2/(P1*(V1+V2))$, wherein V1 is the volume of the sample vial, and V2 is the volume of the gas detection chamber;

S4. Reading the content data of fermentation gases of various intestinal flora in the sample by using a plurality of gas sensors in the gas detection chamber to obtain the concentration C of a certain fermentation gas, and deducing the concentration of the fermentation gas in the sample vial is $C0=C*(P1*(V1+V2))/((P1-P2)*V1)$;

S5. According to step S3, the fermentation gas of gut flora was quantitatively extracted from the sample vial again, so that the proportion of fermentation gas of gut flora in the gas detection chamber reached the second gradient;

S6. Reading the content data of each fermentation gas of gut flora in the gas detection chamber;

S7. Adopting a gradient injection mode, repeating the step S5 and S6 until the detection of all the fermentation gases of gut flora with preset gradients is completed, while the detection data of each fermentation gases of gut flora is within the preset detection range of the gas sensor;

S8. Introducing the filtered air to flush the detection chamber for several times until the reading of each gas sensor returns to zero, which is prepared for the detection of the next sample;

S9. Calculating the concentration of various fermentation gas of gut flora in the fermentation vial according to the acquired data.

Preferably, the fermentation gases of gut flora described in steps S4, S6, and S7 comprise hydrogen, hydrogen sulfide, methane, and carbon dioxide.

Preferably, the proportion of the fermentation gas entering the gas detection chamber in step S3 ranges from 1% to 99%.

Preferably, the fermentation gas entering the gas detection chamber through the gradient injection mode described in step S7 is set to different proportions and injection times.4. Preferably, the gradient injection mode is as described: the fermentation gas is extracted 4 times continuously, each time accounting for 1%, 5%, 10% and 84% of the total fermentation gas.

An instrument for performing the method for detecting composition of fermentation gas of gut flora described in the present invention, wherein the instrument comprises a sample chamber, a sampling mechanism for collecting the sample form sample chamber, and a gas detection chamber for detecting the collected gas samples; and a plurality of gas sensors and second air pressure sensors for a certain fermentation gas of gut flora are arranged in gas detection chamber, and a valve group is arranged between the sampling mechanism and the gas detection chamber in a connection mode, while the sampling mechanism, the gas detection chamber and the valve group is connected by a sealing pipe group; and a first air pressure sensor for detecting the air pressure of sample vial is arranged on the sampling mechanism; and a master control circuit for automatically controlling each mechanism to complete related detection actions is further included in the instrument, the master control circuit is coupled with the control ports of sampling mechanism, gas detection chamber and valve group respectively, and further coupled with the output ports of the first air pressure sensor and that of the second air pressure sensor;

The sample vial is arranged in the sample chamber, the sampling mechanism is provided with a sampling needle toward the sample vial, while the sampling needle is hermetically connected with the sampling mechanism;

The vacuum generator is hermetically connected with the gas detection chamber and the valve group respectively, and the control port of that is coupled with the master control circuit;

The master control circuit sends a starting signal to the vacuum generator while the sample is needed to extract from the sample vial, and the proportion of the fermentation gas of gut flora entering the gas detection chamber is calculated according to the readings of the first air pressure sensor and the second air pressure, the calculation formula is as follow: $(P1-P2)*V2/(P1*(V1+V2))$, wherein V1 is the volume of sample vial, and V2 is the volume of the gas detection chamber;

The master control circuit sends a stop signal to the valve group while the proportion of the fermentation gas of the gut flora entering the gas detection chamber reaches a preset proportion;

The master control circuit deduce the concentration C0 of a certain fermentation gas in the sample vial as $C0=C*(P1*(V1+V2))/((P1-P2)*V1)$ by using the concentration data C of the fermentation gas detected by the sensor, and the C0 is output to the display device: the master control circuit is pre-installed with the gradient injection mode to successively control the proportion of fermentation gas of gut flora entering the gas detection chamber to obtain multiple detection data; for the sample with different gas composition, the detection data which is more conformed with the detection range of the sensor is selected and displayed to the human-machine interface.

The gas sensor comprises a methane sensor, an hydrogen sensor, an hydrogen sulfide sensor or carbon dioxide sensor.

The instrument of the present invention further comprises a shell and a base being butt joint to form a confined space for accommodating various mechanisms; a power switch for starting the equipment and a door switch for opening and closing the sample chamber are arranged on the shell, while the control ports of the power switch and that of the door switch are coupled with the master control circuit.

The instrument of the present invention is provided with an openable first access panel and second access panel on the shell, while the first access panel is arranged corresponding to the position of the gas detection chamber, and the second access panel is arranged corresponding to the position of the valve group.

The present invention mainly solves the following two problems:

1. Accurate detection of each kind of gas component of a small amount of gas mixture (less than 10 ml) is solved.
2. The huge difference of gas component among samples is overcome, so that realizing the wide-range, high-precision and automatic detection.

Compared with the prior art, the beneficial effects of the present invention are as following:

1. The existing environmental gas detection devices are based on the batch fermentation models which are not suitable for gut flora. These devices often require several liters of gas to pump the environmental gas into detection chamber, and the gas content is detected by the sensor while the gas in the detection chamber reaches equilibrium with the environmental gas. Or an enlarged space, such as about 1 meter of optical path, is required in order to utilize a variety of analytical instruments for gas detection, such as gas within a large chimney. In addition, the gas concentration produced by the gut flora is relatively high, which is often exceeded those in the environment. For example, the explosion limit of methane in the environment is 4%, so the detection range of the sensor for environmental gas may be selected with an upper threshold of 4%. The content of methane in the intestinal tract was reported to 7.2% (Leavt, Gastroenterology, 1970), and we would like to obtain relatively accurate data to allow the gas content to be used as a metabolic parameter for biomarker screening. Therefore, the detection of fermentation gas of gut flora cannot be carried out by the environmental gas detection devices.
2. Compared with the batch fermentation model used in the current analysis of the fermentation gas, the sample amount required by the method provided by the present invention is relatively low. Whether the equipment with a 200 mL fermentation container developed by the Australian researchers, or the 250 mL airtight container for the detection of methane and hydrogen sulfide used by the American researcher, the requirement amount of fecal samples is about 10 g, which is very unfavorable for clinical application, especially for patients with small sample volume, such as newborns and diarrhea patients. In the present invention, in-vitro batch fermentation may be performed by using a small amount of fecal samples such as 0.5 g, thereby realizing the analysis of metabolites.

3. The culture medium of the continuous fermentation model is used for batch fermentation models, which may reduce the uncertainty factors of the in-vitro fermentation of gut flora, so that a unified fermentation system is provided to obtain large-scale comparable metabolites data of human gut flora, which lays a methodology foundation for the application of data of in-vitro batch fermentation in clinical and scientific research.
4. The present invention can automatically measure five indicators such as the total amount of fermentation gas and the composition of four kinds of gases at one time, which improves the accuracy and comparability of detection data and lays a solid foundation for the reliability of gas detection of the fermentation system.
5. The present invention adopts a gradient injection method, so that the high-precision and wide-range detection may be simultaneously achieved by a small range/high precision sensor.

The gas sensor is the most widely used for the detection of the environmental gas, and the purpose of the detection of environmental gas is only to determine whether the environmental gas is harmful to the human or has the risk of explosion, so the limit of parameters are all constant, and there has no difficulty in the selection of sensors in environmental gas detection equipment, as long as the threshold value is accurately detected. However, the present invention relates to accurate detection of gas components in a sample, while the difference between various samples is very large, and the content of different gases in same sample may also be at different ranges of the sensor detection range, so that one detection cannot satisfy the range of four gas sensors. Therefore, the application of gradient injection method enables the present invention to be suitable for the detection of most fermentation gas of human gut flora.

6. The composition of fermentation gas and the data of gas production of the fermentation gas corresponding to the SCFA are provided to make up the existing defects of detection of the metabolic product of the gut flora at present, that is, there are only SCFA data for two major types of metabolites, but loss the gas parameters.
7. The automatic detection of fermentation gas is realized by the present invention, which is convenient for application and promotion in multiple fields including clinical.

EMBODIMENTS

Figure 1:
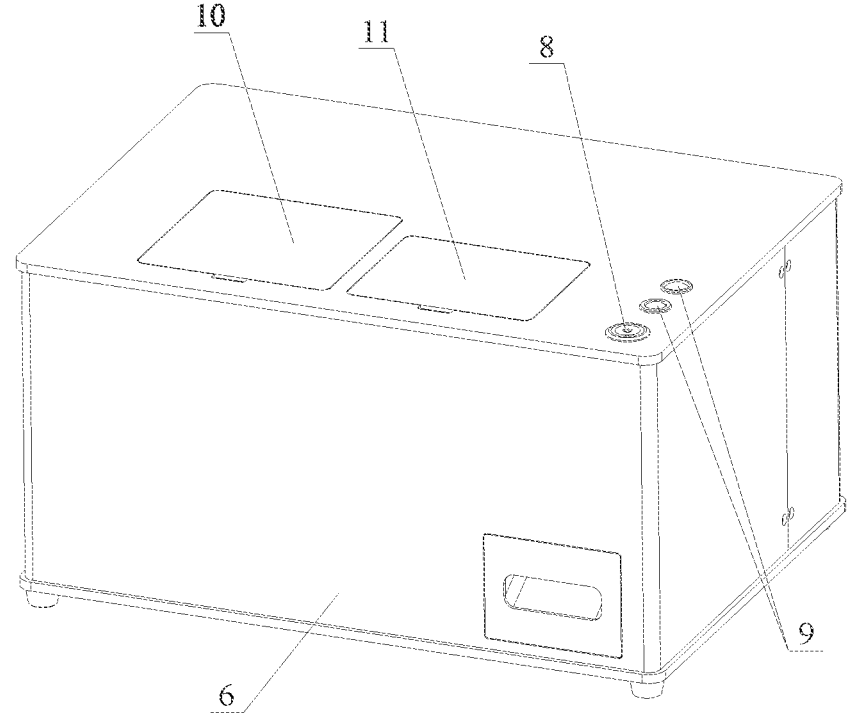
FIG. 1 is a schematic diagram of the appearance of an instrument according to an embodiment of the present invention.
Figure 2:
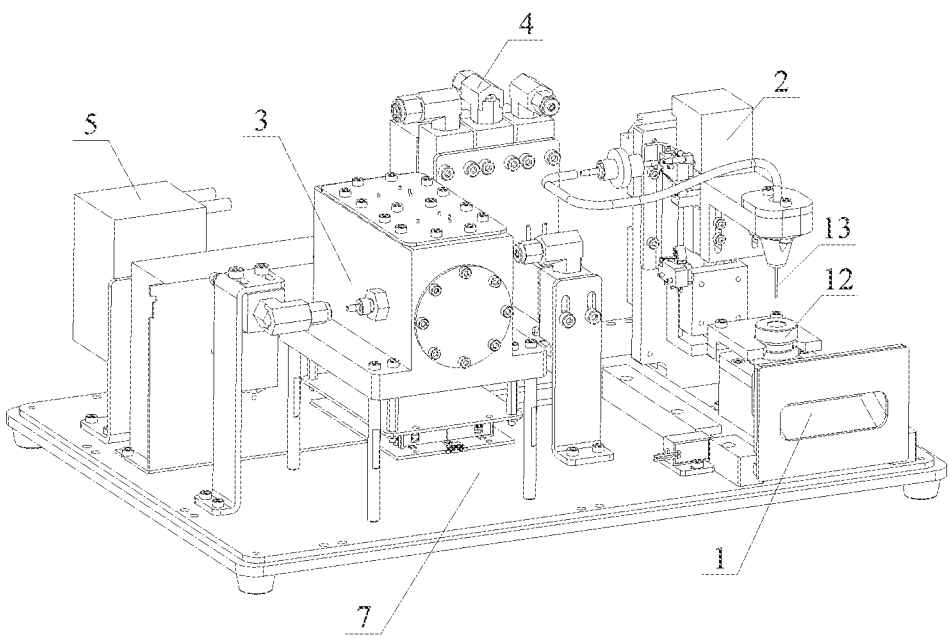
FIG. 2 is a schematic diagram of an internal structure of an instrument according to an embodiment of the present invention.
Figure 3:
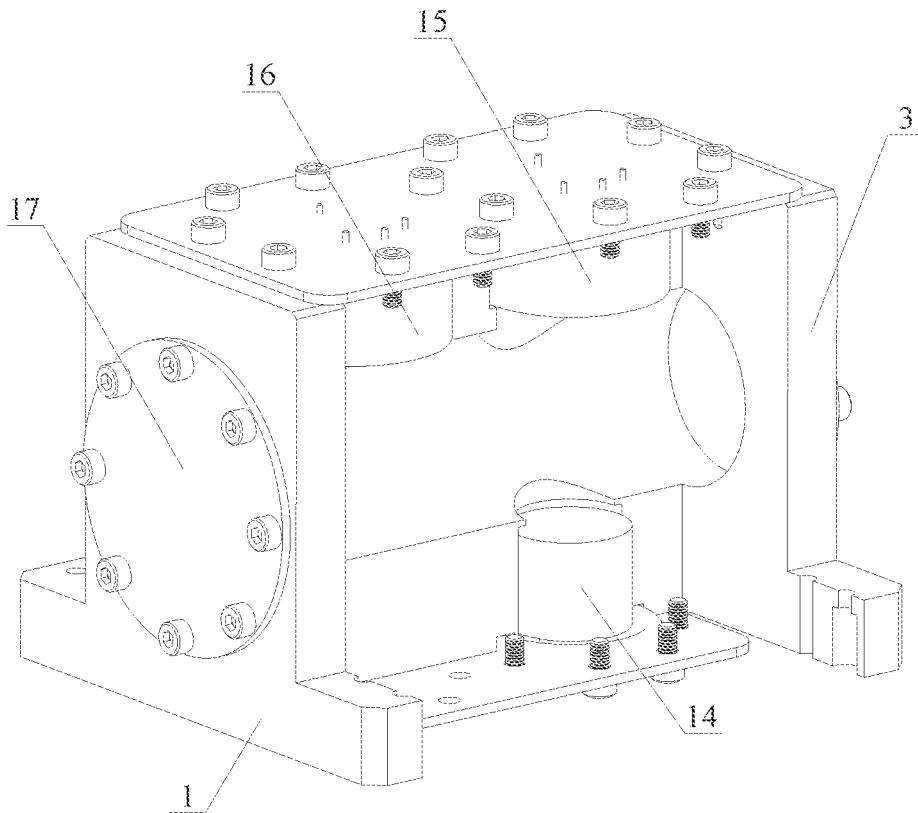
FIG. 3 is a schematic diagram of an internal structure of the gas detection chamber in FIG. 2.

The following description is used to disclose the present invention to enable those skilled in the art to implement the present invention. The preferred embodiments in the following description are by way of example only, and other obvious variations will occur to those skilled in the art. The basic principles of the invention defined in the following description may be applied to other embodiments, modifications, improvements, equivalents, and other technical solutions without departing from the spirit and scope of the invention.

It should be understood by those skilled in the art that, in the disclosure of the present disclosure, the orientation or positional relationship indicated by the terms "longitudinal," "transverse," "upper," "lower," "front," "rear," "left," "right," "vertical," "horizontal," "top," "bottom," "vertical," "horizontal," "top," "bottom," "vertical," "outer," and the like is based on the orientation or positional relationship shown in the accompanying drawings, but is not intended to indicate or imply that the indicated device or element must have a particular orientation to construct and operate in a particular orientation, and therefore, the above terms are not to be construed as limiting the invention.

In the present disclosure, the term "a" in the claims and the description should be understood as "one or more", that is, in one embodiment, the number of one element may be one, and in other embodiments, the number of the elements may be multiple. The term "a" cannot be understood as being unique or single unless the number of elements is explicitly illustrated in the disclosure of the present invention, and the term "a" is not to be construed as a limitation on the number.

In the description of the present disclosure, it should be understood that "first", "second" and the like are only used for descriptive purposes, and cannot be understood as indicating or implying relative importance. In the description of the present disclosure, it should be noted that unless expressly specified and defined otherwise, "connected" and "coupled" shall be construed broadly, for example, may be a fixed connection or a detachable connection or an integrated connection; may be a mechanical connection or an electrical connection; may be a direct connection or an indirect connection via a medium. For those of ordinary skill in the art, the specific meanings of the above terms in the present disclosure may be understood according to specific situations.

In this specification, the description of reference terms of "an embodiment," "some embodiments," "an example," "a specific example," or "some examples" means that a the particular feature, structure, material, or characteristic described in connection with the embodiment or example is included in at least one embodiment or example of the present invention. In this specification, the schematic representation of the above terms does not have to be directed to the same embodiment or example. Furthermore, the particular features, structures, materials, or characteristics described may be combined in any suitable manner in any one or more embodiments or examples. In addition, a person skilled in the art can integrate and combine different embodiments or examples and features of different embodiments or examples described in this specification without contradiction.

A method for detecting composition of fermentation gas of gut flora comprises:

S1. Opening the sample chamber, placing the fermented sample vial into the sample chamber, and closing the sample chamber;

S2. Inserting the sampling needle into the sample vial, detecting the air pressure P0 of the sample vial by using a first air pressure sensor, and converting the total amount of the fermentation gas to $\Delta V = V1(P0/Patm-1)$, wherein V1 is the volume of the sample vial, and the Patm is atmospheric pressure, namely the pressure of the sample vial before fermentation.

S3. The pressure of sample vial reaching the first pressure P1 by using the air pump connected to sample vial, the pressure of gas detection chamber reaching the second pressure P2 by using the vacuum connected to gas detection chamber, and then communicating the sample vial and the gas detection chamber to quantitatively extract the fermentation gas from the sample vial, so that the proportion of the fermentation gas entering the gas detection chamber reaches the first gradient; the proportion of gas entering the gas detection chamber is $(P1-P2)*V2/(P1*(V1+V2))$, wherein V1 is the volume of the sample vial, and V2 is the volume of the gas detection chamber;

S4. Reading the content data of fermentation gases of various intestinal flora in the sample by using a plurality of gas sensors in the gas detection chamber to obtain the concentration C of a certain fermentation gas, and deducing the concentration of the fermentation gas in the sample vial is $C0=C*(P1*(V1+V2))/((P1-P2)*V1)$;

S5. According to step S3, the fermentation gas of gut flora was quantitatively extracted from the sample vial again, so that the proportion of fermentation gas of gut flora in the gas detection chamber reached the second gradient;

S6. Reading the content data of each fermentation gas of gut flora in the gas detection chamber;

S7. Adopting a gradient injection mode, repeating the step S5 and S6 until the detection of all the fermentation gases of gut flora with preset gradients is completed, while the detection date of each fermentation gases of gut flora is within the preset detection range of the gas sensor;

S8. Introducing the filtered air to flush the detection chamber for several times until the reading of each gas sensor returns to zero, which is prepared for the detection of the next sample;

S9. Calculating the concentration of various fermentation gas of gut flora in the fermentation vial according to the acquired data.

The various fermentation gases of gut flora described in steps S4, S6, and S7 include hydrogen, hydrogen sulfide, methane, and carbon dioxide.

The proportion of the fermentation gas entering the gas detection chamber in step S3 ranges from 1% to 99%.

The fermentation gas entering the gas detection chamber through the gradient injection mode described in step S7 is set to different proportions and injection times, for example: the fermentation gas is extracted 4 times continuously, each time accounting for 1%, 5%, 10% and 84% of the total fermentation gas.

An instrument for performing the method for detecting composition of fermentation gas of gut flora described in the present invention, wherein the instrument comprises a sample chamber 1, a sampling mechanism 2 for collecting the sample form sample chamber 1, and a gas detection chamber 3 for detecting the collected gas samples; and a plurality of gas sensors and second air pressure sensors for a certain fermentation gas of gut flora are arranged in gas detection chamber 3, and a valve group 4 is arranged between the sampling mechanism 2 and the gas detection chamber 3 in a connection mode, while the sampling mechanism 2, the gas detection chamber 3 and the valve group 4 is connected by a sealing pipe group; and a first air pressure sensor for detecting the air pressure of sample vial is arranged on the sampling mechanism; and a master control circuit for automatically controlling each mechanism to complete related detection actions is further included in the instrument, the master control circuit is coupled with the control ports of sampling mechanism 2, gas detection chamber 3 and valve group 4 respectively, and further coupled with the output ports of the first air pressure and the second air pressure;

The sample vial 12 is arranged in the sample chamber 1, the sampling mechanism 2 is provided with a sampling needle 13 toward the sample vial 12, while the sampling needle 13 is hermetically connected with the sampling mechanism 2;

The vacuum generator 5 is hermetically connected with the gas detection chamber 3 and the valve group 4 respectively, and the control port of that is coupled with the master control circuit;

The master control circuit sends a starting signal to the vacuum generator 5 while the sample is needed to extract from the sample vial 12, and the proportion of the fermentation gas of gut flora entering the gas detection chamber 3 is calculated according to the readings of the first air pressure sensor and the second air pressure, the calculation formula is as follow: $(P1-P2)*V2/(P1*(V1+V2))$, wherein V1 is the volume of sample vial 12, and V2 is the volume of the gas detection chamber 3; The master control circuit sends a stop signal to the valve group 4 while the proportion of the fermentation gas of the gut flora entering the gas detection chamber 3 reaches a preset proportion;

The master control circuit deduce the concentration C0 of a certain fermentation gas in the sample vial 12 as $C0=C*(P1*(V1+V2))/((P1-P2)*V1)$ by using the concentration data C of the fermentation gas detected by the sensor, and the C0 is output to the display device: the master control circuit is pre-installed with the gradient injection mode to successively control the proportion of fermentation gas of gut flora entering the gas detection chamber 3 to obtain multiple detection data; for the sample with different gas composition, the detection data which is more conformed with the detection range of the sensor is selected and displayed to the human-machine interface.

The gas sensor includes a CH4 sensor, an H2 sensor, an H2S sensor or CO2 sensor.

The instrument of the present invention further comprises a shell 6 and a base 7, which being butt joint to form a confined space for accommodating various mechanisms; a power switch 8 for starting the equipment and a door switch 9 for opening and closing the sample chamber are arranged on the shell, while the control ports of the power switch 8 and the door switch 9 are coupled with the master control circuit.

The instrument of the present invention is provided with an openable first access panel 10 and second access panel 11 on the shell 6, while the first access panel 10 is arranged corresponding to the position of the gas detection chamber 3, and the second access panel 11 is arranged corresponding to the position of the valve group 4.

As shown in FIG. 1 to FIG. 4, an instrument for performing the method for detecting composition of fermentation gas of gut flora comprises a shell 6 and a base 7, which being butt-joint to form a confined space for accommodating various mechanisms, while a sample chamber 1 for placing the gas to-be-detected, a sampling mechanism 2 for quantitatively sampling and collecting samples from the sample chamber 1, a gas detection chamber 3 for detecting the concentration of the collected sample, and a vacuum generator 5 for emptying the sample detection chamber 3 before detection and cleaning up that after detection are sequentially arranged in the shell 6.

A movable sample vial 12 may be placed in the sample chamber 1, an automatic control and movable sampling needle 13 towards the sample vial 12 is connected to the sampling mechanism 2, which are connected through the sealing pipe group for sampling.

A plurality of gas sensors for detecting fermentation gas of gut flora are arranged in the gas detection chamber 3, according to actual detection requirements, sensors such as a $CH_4$ sensor 14, a $H_2$ sensor 15, a $H_2S$ sensor 16, or a $CO_2$ sensor 17 may be included but are not limited to those of which is capable of determining indicators such as respective gas content, air pressure, and temperature.

A valve group 4 capable of controlling gas sample injection time and pressure is connected between the sampling mechanism 2 and the gas detection chamber 3, the gas cavities of the sampling mechanism 2, the gas detection chamber 3 and the valve group 4 are respectively connected through the sealing pipe group, while the vacuum generator 5 is respectively connected with the gas detection chamber 3 and the valve group 4 also through that.

Figure 4:
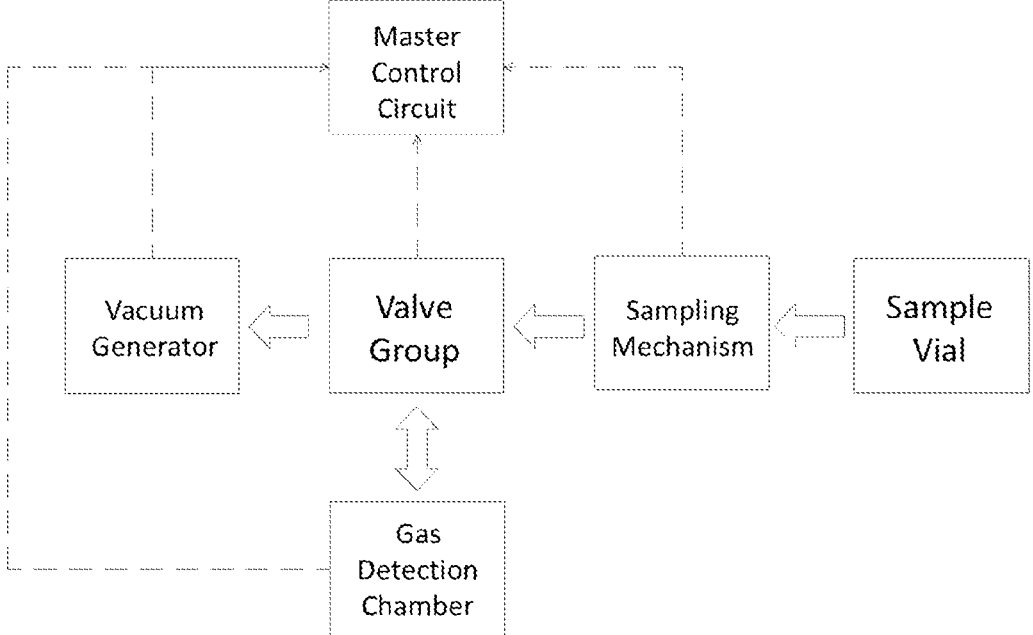
FIG. 4 is a flow chart of a control of an instrument according to an embodiment of the present invention.

As shown in FIG. 4, the shell 6 is further internally provided with a master control circuit, which may automatically controls and program each mechanism to automatically complete all detection actions, while the master control circuit is respectively coupled with the sampling mechanism 2, the gas detection chamber 3, the valve group 4 and the vacuum generator 5 through the wire groups.

The logic structure and the workflow of the present invention are as follows:

1. A certain vacuum state of the gas detection chamber may be adjusted by the vacuum generator through the valve group;
2. The gas enters the instrument from the sample vial by the sampling mechanism, while the sampling volume is adjusted by the valve group;
3. The gas enters the gas detection chamber, which is detected by each gas sensor group;
4. The detection result is calculated by preset software, so the gas content and the gut flora composition in the sample vial are obtained.

The master control circuit controls all component switches, the running time, and the operation.

In the present invention, the in-vitro fermentation model and the instrument are used to directly inoculate the excrement suspension of the subject into the culture medium for in-vitro fermentation, and the sample is pre-stored in the sample chamber, so that the sample is automatically and quantitatively sampled from the sample chamber through the sampling mechanism, and finally the gas component is detected by the gas detection chamber, which may accurately detect the content, the composition and the proportion of each component of the gas produced by the microorganisms at the colon of the subject.

Compared with a respiratory gas tester, the present invention is applicable to a wide range of people, and the detection result of the detected gas is closer to the gas production yield and the components of the colon. With respect to the detection of the components of the flatus, the error generated by the present invention is small and the detection is more convenient.

The shell 6 is provided with a power switch 8 for controlling the starting of the device and a door switch 9 for the opening and closing of the sample chamber 1, while the power switch 8 and the door switch 9 are respectively coupled with the master control circuit through the wire group to realize one-key automatic control operation.

An openable first access panel 10 and second access panel 11 is arranged on the shell 6, while the first access panel 10 is arranged corresponding to the position of the gas detection chamber 3, and the second access panel 11 is arranged corresponding to the position of the valve group 4, which may facilitate the maintenance of the core components and the faulted circuit of the instrument.

The present invention provide an instrument which is specially designed for the fermentation gas production of gut flora of the neonatal necrotizing enterocolitis, compared with the prior art, the content, the composition and the proportion of each component of the gas produced by the microorganisms at the colon of the subject may be more accurately detected by the present invention.

The invention claimed is:

1. A method for detecting composition of fermentation gas of gut flora comprises:

S1. opening a sample chamber, placing a fermented sample vial into the sample chamber, and closing the sample chamber;

S2. inserting a sampling needle into the sample vial, detecting an air pressure P0 of the sample vial by using a first air pressure sensor, and converting the total amount of the fermentation gas to $\Delta V=V1(P0/Patm-1)$, wherein V1 is the volume of the sample vial, and the Patm is atmospheric pressure, namely the pressure of the sample vial before fermentation;

S3. the pressure of sample vial reaching a first pressure P1 by using the air pump connected to sample vial, the pressure of gas detection chamber reaching a second pressure P2 by using the vacuum generator connected to gas detection chamber, and then communicating the sample vial and the gas detection chamber to quantitatively extract the fermentation gas from the sample vial, so that the proportion of the fermentation gas entering the gas detection chamber reaches a first gradient; the proportion of gas entering the gas detection chamber is $(P1-P2)*V2/(P1*(V1+V2))$, wherein V1 is the volume of the sample vial, and V2 is the volume of the gas detection chamber;

S4. reading content data of fermentation gases of various intestinal flora in the sample by using a plurality of gas sensors in the gas detection chamber to obtain a concentration C of a certain fermentation gas, and deducing a concentration of the fermentation gas in the sample vial is $C0=C*(P1*(V1+V2))/((P1-P2)*V1)$;

S5. according to step S3, the fermentation gas of gut flora was quantitatively extracted from the sample vial again, so that the proportion of fermentation gas of gut flora in the gas detection chamber reached the second gradient;

S6. reading the content data of each fermentation gas of gut flora in the gas detection chamber;

S7. adopting a gradient injection mode, repeating the step S5 and S6 until the detection of all the fermentation gases of gut flora with preset gradients is completed, while a detection date of each fermentation gases of gut flora is within the preset detection range of the gas sensor;

S8. introducing a filtered air to flush the detection chamber for several times until the reading of each gas sensor returns to zero, which is preparing for the detection of the next sample;

S9. calculating the concentration of various fermentation gases of gut flora in the fermentation vial according to the acquired data.

2. The method for detecting composition of fermentation gas of gut flora according to claim 1, wherein the fermentation gases of gut flora described in steps S4, S6, and S7 comprise hydrogen, hydrogen sulfide, methane, and carbon dioxide.

3. The method for detecting composition of fermentation gas of gut flora according to claim 1, wherein the proportion of the fermentation gas entering the gas detection chamber in step S3 ranges from 1% to 99%.

4. The method for detecting composition of fermentation gas of gut flora according to claim 1, wherein the fermentation gas entering the gas detection chamber through the gradient injection mode described in step S7 is set to different proportions and injection times.

5. The method for detecting composition of fermentation gas of gut flora according to claim 4, wherein the gradient injection mode is as described: the fermentation gas is extracted 4 times continuously, each time accounting for 1%, 5%, 10% and 84% of the total fermentation gas.

6. An instrument for performing the method for detecting composition of fermentation gas of gut flora according to claim 1, wherein the instrument comprises a sample chamber, a sampling mechanism for collecting the sample form sample chamber, and a gas detection chamber for detecting the collected gas samples; and a plurality of gas sensors and second air pressure sensors for a certain fermentation gas of gut flora are arranged in gas detection chamber, and a valve group is arranged between the sampling mechanism and the as detection chamber in a connection mode while the sampling mechanism the gas detection chamber and the valve group is connected by a sealing pipe group; and a first air pressure sensor for detecting the air pressure of sample vial is arranged on the sampling mechanism; and a master control circuit for automatically controlling each mechanism to complete related detection actions is further included in the instrument, the master control circuit is coupled with the control ports of sampling mechanism, gas detection chamber and valve group respectively, and further coupled with the output ports of the first air pressure sensor and that of the second air pressure sensor;

the sample vial is arranged in the sample chamber, the sampling mechanism is provided with a sampling needle toward the sample vial, while the sampling needle is hermetically connected with the sampling mechanism;

the vacuum generator is hermetically connected with the gas detection chamber and the valve group respectively, and the control port of that is coupled with the master control circuit;

the master control circuit sends a starting signal to the vacuum generator while the sample is needed to extract from the sample vial, and the proportion of the fermentation gas of gut flora entering the gas detection chamber is calculated according to the readings of the first air pressure sensor and the second air pressure, the calculation formula is as follow: $(P1-P2)*V2/(P1*(V1+V2))$, wherein V1 is the volume of sample vial, and V2 is the volume of the gas detection chamber;

the master control circuit sends a stop signal to the valve group while the proportion of the fermentation gas of the gut flora entering the gas detection chamber reaches a preset proportion;

the master control circuit deduce the concentration C0 of a certain fermentation gas in the sample vial as C0=C*

US 12,565,636 B2

17

(P1\*(V1+V2))/((P1−P2)\*V1) by using the concentration data C of the fermentation gas detected by the sensor, and the C0 is output to the display device: the master control circuit is pre-installed with the gradient injection mode to successively control the proportion of fermentation gas of gut flora entering the gas detection chamber to obtain multiple detection data; for the sample with different gas composition, the detection data which is more conformed with the detection range of the sensor is selected and displayed to the human-machine interface.

7. The instrument according to claim 6, wherein the gas sensor comprises a methane sensor, a hydrogen sensor, a hydrogen sulfide sensor or carbon dioxide sensor.

8. The instrument according to claim 7, wherein the instrument of the present invention further comprises a shell and a base being butt joint to form a confined space for accommodating various mechanisms; a power switch for starting the equipment and a door switch for opening and closing the sample chamber are arranged on the shell, while the control ports of the power switch and that of the door switch are coupled with the master control circuit.

9. The instrument according to claim 8, wherein the shell is provided with an openable first access panel and second access panel, while the first access panel is arranged corresponding to the position of the gas detection chamber, and the second access panel is arranged corresponding to the position of the valve group.

\* \* \* \* \*